US006966321B2

(12) United States Patent
Hess

(10) Patent No.: US 6,966,321 B2
(45) Date of Patent: Nov. 22, 2005

(54) METHOD AND DEVICE FOR STABILIZING A PATIENT'S HEAD ON A SPINE BOARD

(76) Inventor: Michael T. Hess, 3152, Forest Knoll La., Langley, WA (US) 98260

( * ) Notice: Subject to any disclaimer, the term of this patent is extended or adjusted under 35 U.S.C. 154(b) by 183 days.

(21) Appl. No.: 10/695,926

(22) Filed: Oct. 28, 2003

(65) Prior Publication Data

US 2004/0084053 A1    May 6, 2004

Related U.S. Application Data

(60) Provisional application No. 60/421,891, filed on Oct. 28, 2002.

(51) Int. Cl.[7] .................................................. A61F 5/37
(52) U.S. Cl. ....................... 128/870; 128/869; 128/846; 5/628; 5/637
(58) Field of Search ............................. 128/845, 846, 128/869, 870; 5/626, 628, 630, 636, 637

(56) References Cited

U.S. PATENT DOCUMENTS

| 3,358,141 | A |  | 12/1967 | Hoffman et al. ............... 250/50 |
| 3,469,268 | A |  | 9/1969 | Phillips ........................... 5/82 |
| 3,724,453 | A |  | 4/1973 | Dixon et al. ............... 128/87 R |
| 3,737,923 | A |  | 6/1973 | Prolo .............................. 5/82 |
| 4,034,748 | A |  | 7/1977 | Winner ..................... 128/87 R |
| 4,124,908 | A |  | 11/1978 | Burns et al. .................. 5/82 R |
| 4,151,842 | A |  | 5/1979 | Miller ......................... 128/87 |
| 4,182,322 | A |  | 1/1980 | Miller ........................ 128/133 |
| 4,297,994 | A |  | 11/1981 | Bashaw ...................... 128/133 |
| 4,473,912 | A |  | 10/1984 | Scheidel et al. ............... 5/82 R |
| 4,905,712 | A |  | 3/1990 | Bowlin et al. ............... 128/870 |
| 5,211,185 | A |  | 5/1993 | Garth et al. ................. 128/870 |
| 5,265,625 | A |  | 11/1993 | Bodman ...................... 128/869 |
| 5,337,760 | A |  | 8/1994 | Nichols ....................... 128/845 |
| 5,360,393 | A | * | 11/1994 | Garth et al. .................. 602/17 |
| 5,435,323 | A |  | 7/1995 | Rudy .......................... 128/870 |
| 5,657,766 | A |  | 8/1997 | Durham ...................... 128/870 |
| 5,967,144 | A | * | 10/1999 | Reynolds ..................... 128/869 |
| 5,988,173 | A | * | 11/1999 | Scruggs ....................... 128/870 |
| 6,170,486 | B1 |  | 1/2001 | Islava .......................... 128/869 |
| 6,230,712 | B1 | * | 5/2001 | Køhnke ....................... 128/869 |
| 6,244,270 | B1 | * | 6/2001 | Lutian et al. ............... 128/869 |
| 6,637,057 | B2 | * | 10/2003 | Phillips et al. .................. 5/637 |
| 6,659,104 | B2 | * | 12/2003 | Kiefer et al. ............... 128/870 |

* cited by examiner

Primary Examiner—Henry Bennett
Assistant Examiner—Camtu Nguyen
(74) Attorney, Agent, or Firm—Garrison & Associates PS; David L. Garrison

(57) ABSTRACT

A device for stabilizing a patient's head on a spine board while allowing longitudinal and rotational movement in conjunction with the body and a method of use for the device are disclosed. The device is comprised of a head harness, a forehead strap, a chin strap, a crown strap and a lateral stabilization strap. The head harness has a skid plate, located on the side of the head harness that rests on a spine board, that is adapted for low friction engagement with the spine board. A patient in a cervical collar is placed on a spine board, the head harness is positioned beneath the patient's head and attached to the spine board. The forehead strap, chin strap, and crown strap are attached to the head harness. The lateral stabilization strap is then attached to the head harness and the attaching straps.

7 Claims, 4 Drawing Sheets

METHOD AND DEVICE FOR STABILIZING A PATIENT'S HEAD ON A SPINE BOARD

CROSS REFERENCE TO RELATED APPLICATION

This application claims the benefit of U.S. Provisional Application Ser. No. 60/421,891, entitled Immobilization Device and Method to Safely Permit Transportation of Accident Victims, filed Oct. 28, 2002.

FIELD OF THE INVENTION

The current invention is related to head or cervical immobilization devices and apparatus. Particularly, the current invention discloses a device to minimize or eliminate the potential for additional injury, during transportation, to a person who suffered traumatic injury to the head, neck or spine region. The device restricts lateral and elevating movement but allows the head to move with the body longitudinally up and down a rigid spine board or rotate off axis longitudinally in direct conjunction with the body. A method of use for the device is also disclosed.

BACKGROUND OF THE INVENTION

When a person receives a traumatic injury, the person's survival often depends upon rapid attention from emergency medical personnel followed by immediate transfer to a properly equipped medical facility. The personnel who are first at the scene of the injury are responsible for treating any immediately life threatening injuries and for stabilizing the patient for immediate transport to the medical facility. Some of the most vexing injuries faced by emergency medical personnel are those involving the neck and back. If the spine is damaged, the very act of moving the patient may exacerbate the problem and lead to more extensive spinal injury. Without radiographs, it is impossible to determine the extent, if any, of damage.

In the past, there has been some controversy over the best way to treat these injuries prior to transport. Some authorities have recommended immobilizing the neck and back in the orientation in which the injured person was found. Other authorities favored moving the patient into a neutral position prior to immobilization. Today, most practitioners follow the second option and immobilize the patient in the neutral position.

A number of devices and procedures have been developed to immobilize victims in a neutral position prior to transport.

U.S. Pat. No. 6,170,486, issued to Islava, and U.S. Pat. No. 5,657,766, issued to Durham show the use of foam blocks positioned on either side of a patient's head and secured to a spine board, typically with hook-loop tape. Generally, at least one strap secures the patient's head against the foam blocks, thereby attempting to immobilize the head. The disclosure in U.S. Pat. No. 5,211,185, issued to Garth et al., and U.S. Pat. No. 4,182,322, issued to Miller, teach the use of devices having pillows or pads that are wrapped around a patient's head and secured to the spine board, again attempting to immobilize the head.

Still other devices, such as those disclosed in U.S. Pat. No. 4,151,842, issued to Miller and U.S. Pat. No. 3,469,268, issued to Phillips, disclose strapping a patient's head directly to the spine board such that it is completely immobilized. U.S. Pat. No. 3,737,923, issued to Prolo, and U.S. Pat. No. 5,435,323, issued to Rudy, disclose securing a patient's head to a device that is fastened to a spine board with mechanical fasteners.

The arrangement disclosed in Rudy secures the head to the device at a single point near each side of the spine board, a pad for supporting the head is fixed to the device which is attached to the spine board with mechanical fasteners. Although the head can move slightly longitudinally relative to the device, the device cannot move relative to the spine board.

U.S. Pat. No. 4,473,912, issued to Scheidel et al., and U.S. Pat. No. 4,297,994, issued to Basha disclose head restraining devices in which the head support device is not fixedly attached to a spine board. Sheidel discloses the use of two adjustable straps extending outward from the head restraint device and attaching to the side of the spine board to provide single point lateral stability. Basha discloses the use of four straps, one at each corner of the device, the straps are elastic and therefore allow some motion in all directions. Both Sheidel and Basha include the use of a longitudinal tension strap for applying traction to the head thereby limiting any downward longitudinal motion. Both devices use a forehead strap and a chin strap to secure the patient's head to the device. Sheidel also discloses the use of a contoured head pad, but it does not conform to the patient's head when the straps are secured. The device disclosed in Basha has a large surface area providing high friction between it and the spine board when it is secured to the spine board by elastic straps. Therefore, it is unlikely that the device of Basha would move as the patient's body normally shifts slightly during transport. The Sheidel device is much smaller and preferably made of an elastomeric urethane foam. Such material is not very slippery and would probably not readily move relative to the board.

The common factor in most of these devices is the simple expedient of firmly attaching the patient to the surface of a stiff board "spine board" which acts as a stretcher to allow the patient to be carried without allowing any flexing of the patient's potentially injured back or neck. This is generally accomplished by firmly securing the head to the spine board, such that the position of the head will not change or shift during transport While the devices of the prior art work to completely immobilize the head of a patient during transportation to a medical facility, they do not address the inevitable resulting compression of the cervical spine when the body of the patient shifts during transportation to such a facility. Failure to address such compression can cause unnecessary pain to a patient as his or her body shifts during such transportation, it can further exacerbate an already existing injury, or in the worst case, it could cause an injury to a previously uninjured patient who is strapped to a spine board as a precautionary measure.

Therefore, there exists a need for a device or appliance to be utilized in case of a suspected or actual cervical spine injury that stabilizes a patient's head on a spine board in a manner restricting lateral and elevating movement, while allowing the head to move with the body longitudinally up and down the spine board, and rotate off axis longitudinally in direct conjunction with the body as it shifts during transport. Such a device that is disposable and easy to use is a significant advance over the prior art.

SUMMARY OF THE INVENTION

Accordingly, it is an object of this invention to provide a device that minimizes or eliminates the potential for additional injury during transportation by stabilizing the head of a patient on a spine board in a manner that restricts lateral and elevating movement, while allowing the head to move with the body longitudinally up and down the spine board.

It is a further object of this invention to provide such a device that allows the head to rotate off axis longitudinally in direct conjunction with the patient's body.

Another object of the current invention is to provide such a device that is disposable.

A yet further object of the current invention is to provide such a device that easy to use.

A still further object of the current invention is to provide such a device that gives the patient the maximum possible comfort during transportation.

Another object of the current invention is to provide such a device that is relatively inexpensive.

The current invention discloses a device that meets the objects above and a method for using the device. The device comprises five basic parts, a head harness, a forehead strap, a lateral stabilization strap, a chin strap, and a crown strap.

The head harness is a multifunction element, it is ergonomically shaped, such that it envelops each side of the head when in use. On the side of the head harness, nearest the spine board is a skid plate that is designed and configured to move relative to the board. The movement of the skid plate serves to allow the head to travel in conjunction with the body as it shifts or rotates during transport. On the side of the head harness nearest the patient and directly opposite the skid plate, is a head pad. Two flexible narrow attachment straps provide point attachment of the harness to both lateral edges of the spine board.

The forehead strap is used to secure the patient's head to the head harness. The forehead strap is a narrow, flexible strap that is secured to the patient's forehead and connected to either side of the head harness.

The lateral stabilization strap is a flexible narrow strap that prevents lateral and elevation movement of the head. The lateral stabilization strap is connected to the forehead strap, and the ends of the lateral stabilization strap are connected to the head harness straps where they meet the lateral sides of the spine board.

The chin strap is a long, narrow strap for securing the patient's chin during transport. The ends of the chin strap are connected to the sides of the head harness.

The crown strap secures the top of the head to each side of the head harness during transport. The ends of the crown strap are also connected to the sides of the head harness.

Once the need to secure a patient to the spine board is determined, a medically approved cervical collar is placed on a patient's neck and the patient is positioned on the spine board. The head harness is placed beneath the patient's head and aligned with the skid plate down and the straps for attaching the head harness to the spine board at the level of the patient's eyes. The head harness is then attached to the spine board and the length of the forehead strap is determined.

The forehead strap is adjusted to the appropriate length and then it is attached to the sides of the head harness, such that the head harness is held on the patient's head. The chin strap is looped under the chin cup portion of the cervical collar and the ends are attached to the head harness. The crown strap is then positioned at the center of the crown of the patient's head, and the ends of the crown strap are attached to the sides of the head harness. The center of the lateral stabilization strap is then attached to the middle of the forehead strap. The ends of the lateral stabilization strap are firmly but gently attached to the end of the head harness lateral straps at the point where they meet the edge of the spine board.

Once the patient is further secured to the spine board, transportation to the hospital can begin. The device of the current invention serves to minimize or eliminate the potential for further injury by stabilizing the patient's head on the spine board. Lateral and elevating movement of the head are prevented by the device, while the patient's head can move longitudinally and rotate off of the longitudinal axis in conjunction with the body.

BRIEF DESCRIPTION OF THE DRAWINGS

The objects and features of the present invention, which are believed to be novel, are set forth in the appended claims. The present invention, both as to its organization and manner of operation, together with further objects and advantages, may best be understood by reference to the following description, taken in conjunction with the accompanying drawing figures, wherein:

BEST MODE OF CARRYING OUT THE INVENTION

Figure 1:
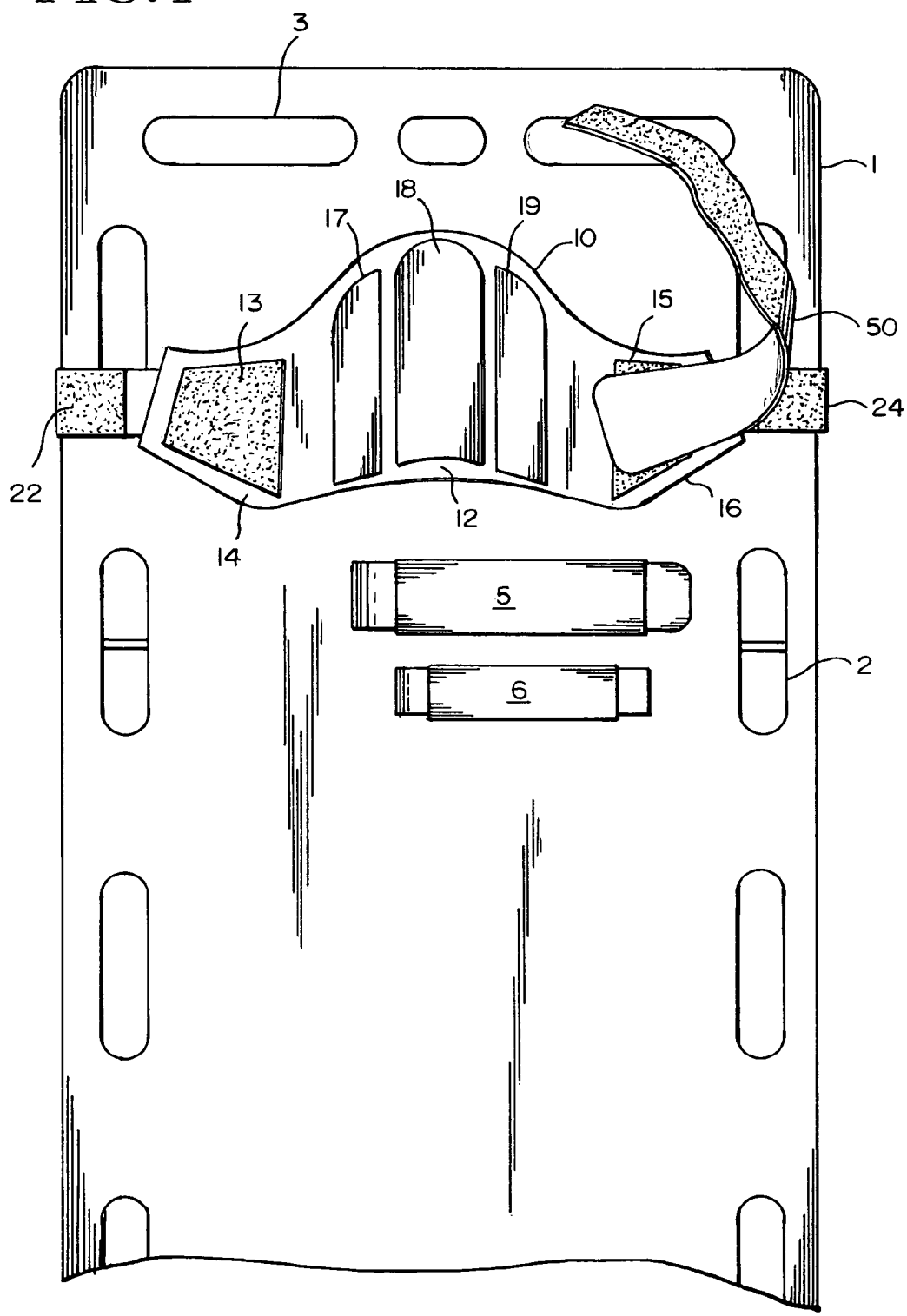
FIG. 1 shows the components of the device disclosed herein on a spine board.

Turning now to the drawings, the devices that are the subject of the current application will be described in preferred embodiments by reference to the numerals of the drawing figures wherein like numbers indicate like parts.

FIG. 1 shows a preferred embodiment of a device that is the subject of the current application. The device is comprised of the head harness 10, the forehead strap 50, and strap packets 5 and 6, which contain a chin strap, a crown strap, and a lateral stabilization strap.

The spine board 1, is a rigid, generally rectangular shaped board constructed from wood or other suitable material. Most spine boards have a plurality of elliptical openings 2 along the lateral edges and a plurality of elliptical openings 3 at each end. These elliptical openings function as hand holds when a patient is being transported.

The head harness 10 of the depicted embodiment is ergonomically shaped and is designed to support a patient's head as he or she lies on a spine board. The harness is comprised of a main panel 12 and side panels 14 & 16, which extend laterally from the main panel. When a patient is placed on a spine board with the head harness beneath his or her head, the side panels will cover the side of the patient's head, and forehead strap 50 will be placed across the patient's forehead. In a preferred embodiment, the main panel and side panels are made from the same piece of material, but other embodiments can include head harnesses wherein the side panels are made from separate pieces of material and then attached to the main panel.

The surface of the head harness shown in FIG. 1 will be the interior surface of the harness after a patient is placed on the spine board. Support cushions 17, 18, & 19 provide cushioning support between the patient's head and the spine board. The cushions in a preferred embodiment are made from a closed cell foam material that is permanently attached to the interior surface of the main panel, but other embodiments can include cushions made from other suitable material.

The interior surface of the head harness also includes portions of a hook in loop type fastening material 13 & 15 that are permanently attached to the side panels 14 & 16. In the embodiment depicted, the material on the interior surface of the side panels is the hook portion of the hook in loop type fastening material. It should be noted that where the specification herein identifies the hook or loop portion of a hook in loop type fastening material, the opposite portion is equally suited for use with the device so long as the strap or panel that it is intended to be attached to has an opposite portion of fastening material.

The head harness 10 is attached to the lateral edges of the spine board with a pair of attachment straps 22 & 24 that extend laterally from the main panel. The attachment straps 22 & 24, in conjunction with the lateral stabilization strap (shown as 80 in FIGS. 6 & 7 and described below), prevent lateral movement and elevation of a patient's head during transportation to a medical facility, while allowing rotational and longitudinal motion due to the single point of attachment on each side of the spine board. The loop portion of a hook in loop type fastener (shown as 40 & 42 in FIGS. 3 & 4) located at the ends of the straps, on the surface facing away from the spine board, is used for attachment of the lateral stabilization strap after a patient is placed on the spine board.

Figure 2:
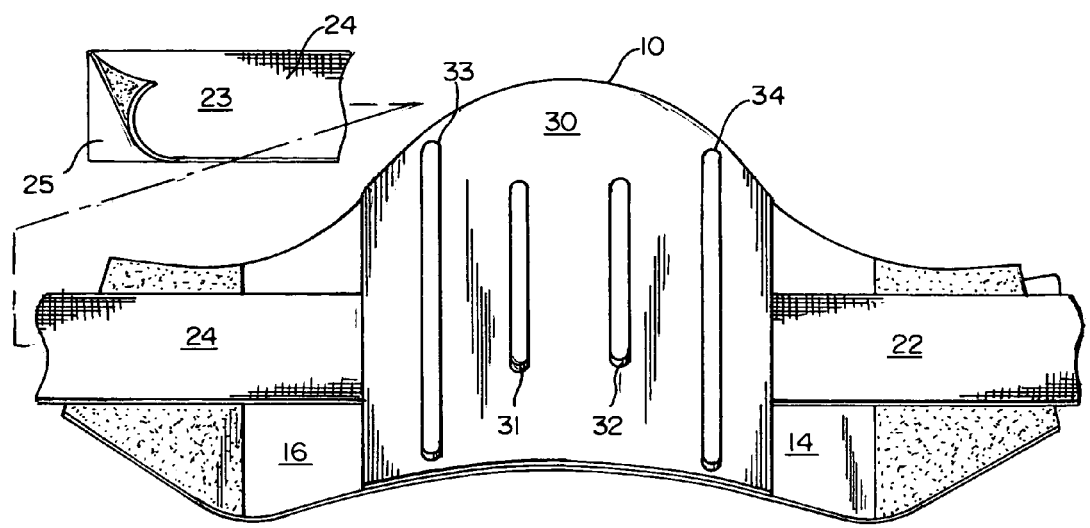
FIG. 2 shows the skid plate and attachment straps of the head harness disclosed herein.

In one preferred embodiment, attachment straps 22 & 24 have a layer of adhesive material at the ends of the straps for attachment to the spine board. Referring to FIG. 2, there can be seen the end of attachment strap 24. The adhesive material 25 is located on the side of the attachment strap that will face the spine board. The adhesive layer 25 is protected by a piece of easily removable material 23 such as a piece of plastic or the like. While not depicted in FIG. 2, the protective cover can have a quick pull tab for ease of removal. The attachment straps are secured to the spine board by removing the protective cover from the adhesive material, placing the adhesive in contact with the spine board at a desired location, and pressing the strap onto the spine board. After transportation of a patient is complete, the attachment straps can be detached from the spine board by pulling up on the end of the straps.

While the embodiment depicted uses a layer of adhesive material to secure the attachment straps to the spine board, other attachment means such as hook in loop fasteners, buckles, quick fit buckles, and snaps can also be used. In at least one preferred embodiment, the attachment straps are 1.5 inches wide and made from vinyl-coated polyester. However, the straps can be constructed of any suitable material, and they can be any width suitable for providing the stability required to eliminate lateral head movement.

Referring again to FIG. 1, the head harness 10 is held in place on a patient's head by a forehead strap 50. The surface of the forehead strap 50 that will face away from a patient's head is covered with the loop portion of a hook in loop type fastening material. The surface of the forehead strap 50 that will be facing a patient's head has a layer of adhesive material similar to the adhesive on the attachment straps. This adhesive is protected by an easily removable cover.

When a patient is placed on the head harness, the person providing medical treatment determines the desired length of the forehead strap 50 and cuts the forehead strap to the desired size. The cover is then removed from the adhesive material on the forehead strap 50, and the center of forehead strap 50 is placed on the center of the patient's forehead such that the strap is adhered to the patient's forehead. The hook in loop type material on the forehead strap 50 is then engaged with the hook in loop materiel 13 & 15 on the interior surface of the side panels 14 & 16.

In at least one preferred embodiment, the portion of the head harness that comprises the main panel 13 and the two side panels 14 and 15 is made from vinyl-coated polyester. However, the head harness can be made from any type of material, with suitable flexibility and strength, that will not become saturated with fluids common at the scene of traumatic events, and disintegrate. Additionally, while the general dimensions of the head harness in at least one preferred embodiment are 5.5 inches by 13.75 inches, other embodiments of the devices can be differently dimensioned so long as the head harness provides suitable stability for the head of a patient placed on a spine board. At least one embodiment of the device disclosed herein is sized to provide stabilization for the head of an infant during transportation to a medical facility.

In at least one preferred embodiment, the forehead strap is a 2 inch by 13 inch strip of vinyl coated polyester, but the strap can be made from any type of material, with suitable flexibility and strength, that will not become saturated with fluids common at the scene of traumatic events, and disintegrate. The forehead strap can also be differently dimensioned so long as it provides an adequate level of adjustment for different head sizes and adequate stability for the head of a patient placed on a spine board.

In at least one preferred embodiment, the side of the forehead strap that faces away from a patient's head is entirely covered with the loop portion of a hook in loop type fastener. The strap is attached to the head harness by mating the loop portion with the hook portion of a hook in loop type fastener that is located on the surface of the side panels that will be facing the patient's head. Other preferred embodiments can utilize other fastening means, such as an adhesive strip along the entire side of the forehead strap facing away from the patient's head, wherein the strip is protected by a cover strip having a tab portion for easy removal, the interior surface of the side panels have smooth surfaces, and the forehead strap is connected to the head harness by use of the adhesive strip.

FIG. 2 depicts the exterior surface of the head harness 10 of a preferred embodiment. The exterior surface of the main panel includes a skid plate 30 that is placed against a spine board when the device is used for stabilizing a patient's head. The skid plate 30 is attached to the back of the main panel of the head harness. The surface of the skid plate that will make contact with the spine board includes a plurality of runners 31, 32, 33, & 34 that are oriented to run parallel to the long axis of the spine board.

The skid plate is constructed from a semi-rigid material having a friction coefficient suitably low such that the skid plate can move longitudinally up and down the spine board and rotate off axis longitudinally in direct conjunction with a patient's body. The use of the skid plate, combined with the single point attachment on each side of the spine board (discussed above), significantly reduces the potential for injury to the patient during transportation.

Also seen in FIG. 2, is the exterior surface of the side panels 14 & 16. This surface includes a portion of a hook in loop type fastening material on each of the side panels for attachment of the chin strap and crown strap (described below).

Figure 3:
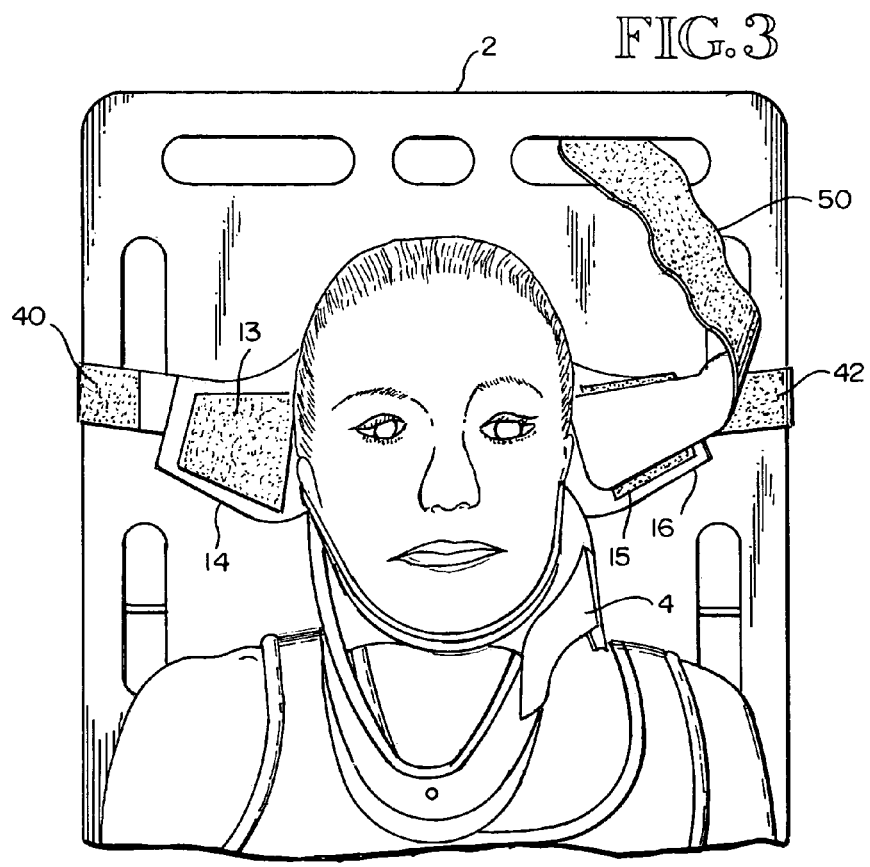
FIG. 3 shows a patient positioned on a head stabilization device, as disclosed herein, that is attached to a spine board.
Figure 4:
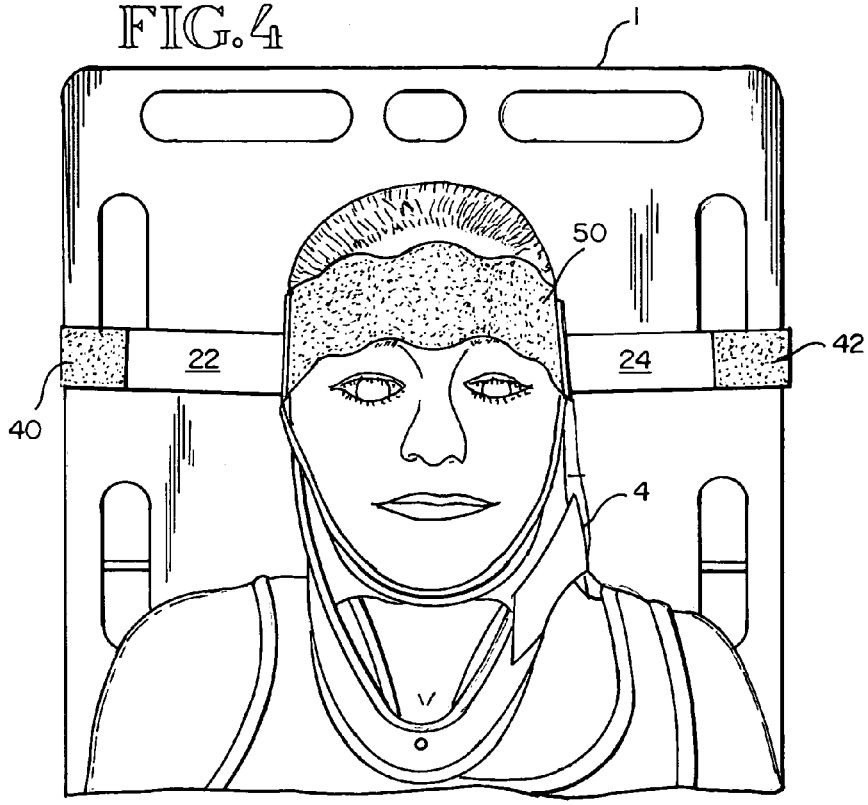
FIG. 4 shows the application and positioning, relative to the patient's head, of the forehead strap of the stabilization device disclosed herein.

FIGS. 3 and 4 illustrate the proper positioning of the device for stabilizing a patient's head during transport and the proper placement of the forehead strap. Once it has been determined that a patient needs to be secured to a spine board, a medically approved cervical collar 4 is placed on the patient's neck and the patient is positioned on a spine board 1. The head harness is placed beneath the patient's head such that the skid plate is facing the spine board and the runners are parallel with the long axis of the spine board.

The head harness is positioned such that the main panel and head cushion are directly beneath the patient's head and the attaching straps 22 & 24 are even with the patient's eyes. The attaching straps are then tightly attached to the lateral edges of the spine board such that the head harness will not move or shift in the lateral direction.

The required length for the forehead strap 50 is determined, and appropriate adjustments are made. One end of the forehead strap 50 is then attached to either of the side panels, the protective cover is removed from the adhesive on the patient side of the strap, and the strap is firmly wrapped around the patient's forehead and attached to the other side panel.

In at least one preferred embodiment of the devices that are the subject of the disclosure herein, the length of the forehead strap is adjusted by simply altering the point along the forehead strap that is initially attached to the side panel of the head harness. In another preferred embodiment, the length of the forehead strap is adjusted by trimming any excess from an end of the forehead strap.

Figure 5:
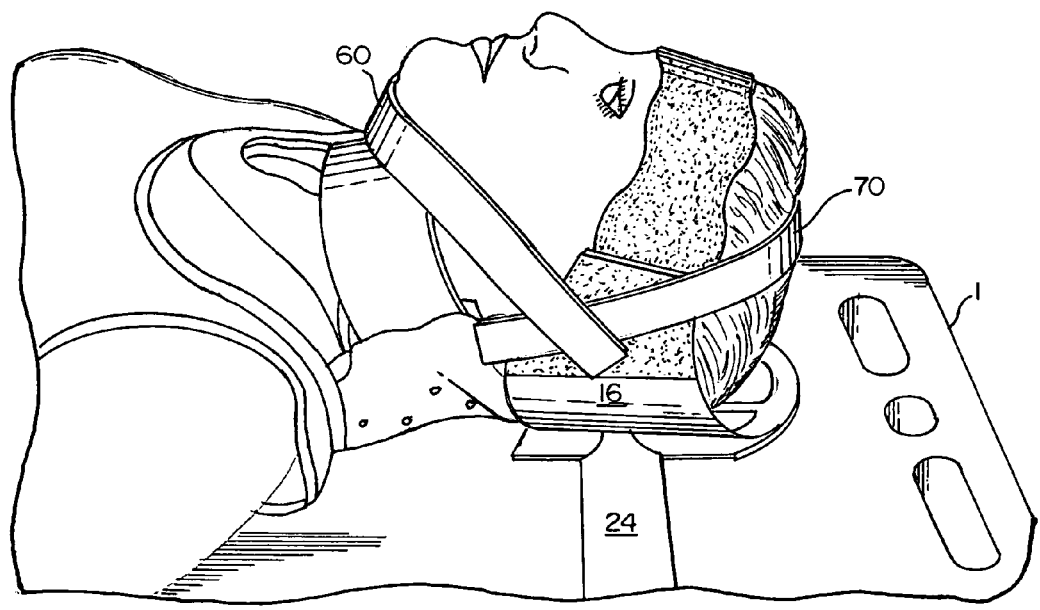
FIG. 5 shows the application and positioning, relative to the patient's head, of the chin strap and crown strap of the stabilization device disclosed herein.

FIG. 5 illustrate the proper placement of the chin strap 60 and the crown strap 70 of the embodiment shown. The chin strap 60 secures the chin and prevents the head from slipping out of the head harness. The chin strap 60 is installed by placing it under the chin portion of the cervical collar 4 and attaching the ends of the chin strap 60 to the exterior surface of the side panels.

The crown strap 70 secures the top of the head and prevents the head from slipping out of the head harness. The crown strap is installed by positioning the strap in the center of the crown of the head and attaching the ends of the strap to the exterior surface of the side panels.

In at least one preferred embodiment, each end of the chin strap and the crown strap each has at least 5 inches of the loop portion, of a hook in loop type fastener, and the ends of the straps are attached to the head harness by mating the loop portion with the hook portion of a hook in loop type fastener that is located on the surface of the side panels facing away from the patient's head. In another preferred embodiment, one side of the chin strap and crown strap are covered entirely with the loop portion of a hook in loop type fastening material. Other preferred embodiments can utilize other fastening means, such as a layer of adhesive material, as described above, located at the ends of the straps, wherein the side of the head harness facing away from the patient's head has a smooth surface, and the straps are connected to the head harness by use of the adhesive.

Figure 6:
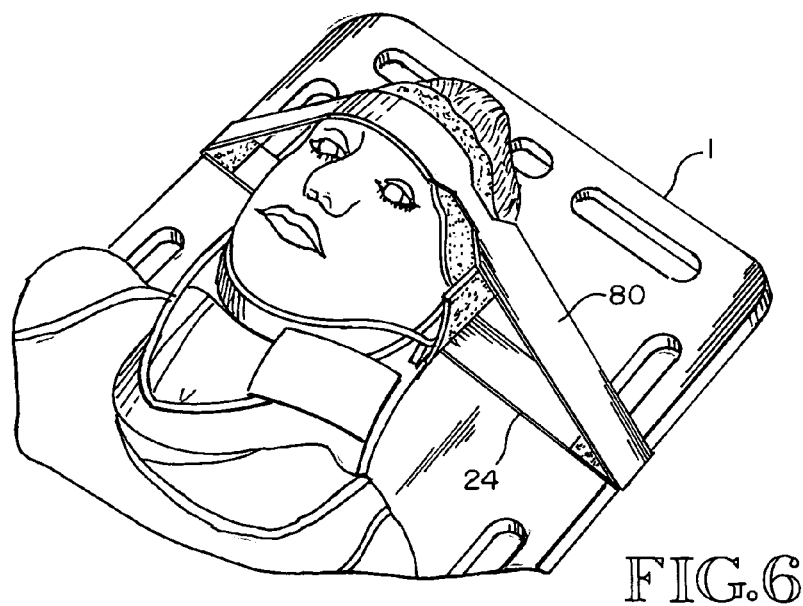
FIG. 6 shows the application and positioning, relative to the patient's head, of the lateral stabilization strap of the device disclosed herein.

FIG. 6 shows the proper placement of the lateral stabilization strap 80 of the depicted embodiment. The lateral stabilization strap 80 prevents lateral and elevation movement of a patient's head during transport. When the lateral stabilization strap 80 is attached to the forehead strap 50, a patient is also prevented from rotating his or her head to face the sides of the spine board.

In at least one preferred embodiment, one surface of the lateral stabilization strap will have at least 4.5 inches of the hook portion of a hook in loop type fastener at the center of the long axis of the strap and at least 7 inches of the hook portion of a hook in loop type fastener at each end of the strap. Other preferred embodiments of the strap can use different fastening means similar to those described above for the chin strap and crown strap.

The lateral stabilization strap 80 is installed by connecting the hook portion of the fastener on the center of the lateral stabilization strap 80 to the loop portion of the fastener on the surface of the forehead strap facing away from the patient, in the middle of the forehead. The ends of the lateral stabilization strap are then connected to the head harness attaching straps 22 & 24 by mating the hook portion of the fastener on the ends of the lateral stabilization strap 80 with the loop portion, on the upper surface of the attaching straps at the edge of the spine board (shown in FIGS. 3 & 4 as 40 & 42).

Other methods of connection can also be used for the lateral stabilization strap, such as adhesive material as described above for connection to the forehead strap and the attachment straps, or the use of buckles for attaching the ends of the lateral stabilization strap to the attachment straps.

In at least one preferred embodiment, the lateral stabilization strap is a 2 inch by 33 inch piece of vinyl-coated polyester, and the chin and crown straps are each 1 inch by 16 inch pieces of vinyl-coated polyester. However, all of these straps can be constructed from any material, with suitable flexibility and strength, that will not become saturated and disintegrate. The straps can also be differently dimensioned so long as they provide an adequate level of adjustment for different head sizes and adequate stability for the head of a patient placed on a spine board.

Figure 7:
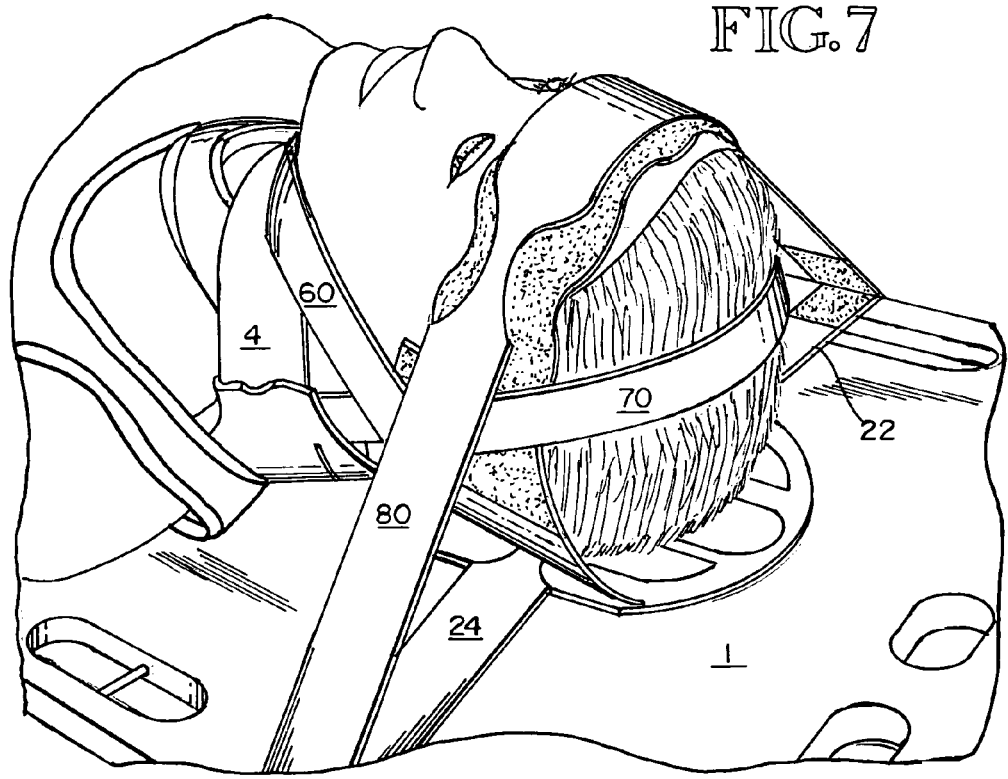
FIG. 7 shows a patient on a spine board, with the patient's head secured by the device disclosed herein.

FIG. 7 shows the depicted preferred embodiment being used to stabilize a patient's head on a spine board. The method for installing the preferred embodiment shown in FIG. 7 would comprise the following general steps:

(1) Determine the need to secure a patient to a spine board.
(2) Place a medically approved cervical collar 4 on the patient's neck.
(3) Position the patient on the spine board 1.
(4) Place the head harness beneath the patient's head such that the skid pad is facing the spine board 1 and the attachment straps 22 & 24 are at the level of the patient's eyes.
(5) Remove the cover slips from the adhesive material at each end of the attachment straps 22 & 24 and attach the head harness to the spine board by wrapping the end of the straps around the edges of the spine board to the other side of the board.
(6) Determine the needed length of the forehead strap 50, adjust the strap to the appropriate length and attach one end of the strap to the side panel on either side of the patient's head by mating the loop portion of the fastener to the hook portion that located on the surface of the side panel facing the patient's head.
(7) Remove the cover slip from the adhesive on the forehead strap 50, firmly wrap the forehead with the forehead strap 50, and attach the free end of the forehead strap to the other side panel.
(8) Place the chin strap 60 around the chin portion of the cervical collar 4 and attach the ends of the strap to the side panels of the head harness with the hook in loop type fastener.

(9) Position the crown strap 70 in the center of the crown of the patient's head and attach the ends to each side of the head harness with the hook in loop type fastener.

(10) Center the loop portion of the fastener on the lateral stabilization strap 80 on the middle of the forehead and firmly but gently connect each end to the attaching straps 22 & 24 using the hook in loop type fastener.

The current application discloses a device that minimizes or eliminates the potential for further injury to a patient while the patient is being transported. This is accomplished by stabilizing the head of a patient on a spine board in a manner that restricts lateral and elevating movement, but allows the head to move with the body longitudinally up and down the spine board, and to rotate off axis longitudinally in direct conjunction with the body. The devices disclosed in the current application are disposable, easy to use, provide comfort to a patient being transported, and are relatively inexpensive to make.

In compliance with the statute, the invention has been described in language more or less specific as to structural features. It is to be understood, however, that the invention is not limited to the specific features shown or described, since the means and construction shown or described comprise preferred forms of putting the invention into effect. Additionally, while this invention is described in terms of being used for stabilizing a patient's head for transportation to a medical facility, it will be readily apparent to those skilled in the art that the invention can be adapted to other uses as well, and therefore the invention should not be construed as being limited to transportation of trauma victims. The invention is, therefore, claimed in any of its forms or modifications within the legitimate and valid scope of the appended claims, appropriately interpreted in accordance with the doctrine of equivalents.

INDUSTRIAL APPLICABILITY

The devices disclosed herein are applicable in the field of devices related to head or cervical immobilization and stabilization. Particularly, the current application discloses devices that can be used to minimize or eliminate the potential for additional injury, during transportation, to a person who suffered traumatic injury to the head, neck or spine region. Also, disclosed is a method of use for such devices. The devices restrict lateral and elevating movement but allow the head to move with the body longitudinally up and down a rigid spine board or rotate off axis longitudinally in direct conjunction with the body. The devices are disposable, easy to use, provide comfort to a patient being transported, and are relatively inexpensive to make.

What is claimed is:

1. A device for stabilizing a patient's head on a spine board comprising:
   a head harness having an interior surface and an exterior surface;
   the head harness further having a main panel, two side panels each extending laterally from the main panel such that one side panel extends from each side of the main panel, two attachment straps each extending laterally from the head harness, a support cushion on the interior surface of the main panel, and a skid plate on the exterior surface of the main panel;
   each of the attachment straps being secured to the head harness and having a free end opposite the main panel of the head harness;
   the skid plate having a plurality of runners running longitudinally along the lower surface of the skid plate and the runners being adapted for low friction engagement with a
   spine board;
   a forehead strap;
   a chin strap;
   a crown strap;
   a lateral stabilization strap;
   a layer of adhesive covering an area at the free end of the attachment straps on the lower surface of the attachment straps, the layer of adhesive having an easily removable protective cover such that the cover can be removed from the layer of adhesive on each attachment strap, and the ends of the attachment strap can be temporarily secured to a spine board by placing the adhesive material in contact with the spine board and applying pressure to the attachment straps;
   a portion of hook in loop material located on the interior surface of the side panels and hook in loop material located on the surface of the forehead strap that will not be facing the forehead of a patient on a spine board, such that the hook in loop material on the interior surface of the side panels can be engaged with the hook in loop material on the forehead strap;
   a layer of adhesive material located on the surface of the forehead strap that will not be facing the forehead of a patient on a spine board, the layer of adhesive having an easily removable protective cover the cover can be removed from the layer of adhesive material and the forehead strap can be temporarily secured to a patient's forehead by firmly placing the adhesive material in contact with the patient's forehead;
   a portion of hook in loop material located on the exterior surface of the side panels and a portion of hook in loop material located at the ends of the chin strap on the surface of the chin strap that will be facing a patient on a spine board, such that the hook in loop material on the exterior surface of the side panels can be engaged with the hook in loop material on the chin strap;
   a portion hook in loop material located at the ends of the crown strap on the surface of the crown strap that will be facing a patient on a spine board, such that the hook in loop material on the lower surface of the side panels can be engaged with the hook in loop material on the crown strap;
   a portion of hook in loop material located on the surface of the lateral stabilization strap that will be facing the forehead of a patient on a spine board, such that the hook in loop material on the lateral stabilization strap can be engaged with the hook in loop material on the forehead strap;
   a portion of hook in loop material located at the ends of the lateral stabilization strap on the surface of the lateral stabilization strap that will be facing the forehead of a patient on a spine board and a portion of hook in loop material located at the free end of the attachment straps on the upper surface of the attachment straps, such that the hook in loop material on the lateral stabilization strap can be engaged with the hook in loop material on the forehead strap;
   whereby when a patient wearing a cervical collar, with a chin cup, is located on a spine board, the head harness is positioned under the patient and attached to the spine board, the forehead strap is secured to the patient's forehead and attached to the head harness, the chin strap is routed across the chin cup of the cervical collar and attached to the head harness, the crown strap is routed across the crown of the patient's head and attached to the head harness; and the lateral stabilization strap is attached to the forehead strap and the attachment straps the patient's head cannot move laterally or be elevated, but the patient's head can move longitudinally or rotate off of the longitudinal axis in conjunction with the patient's body.

2. The device of claim 1 wherein the head harness, the attachment straps, the chin strap, the crown strap, and the lateral stabilization strap are made from vinyl-coated polyester.

3. The method of stabilizing the head of a patient on a spine board comprising the steps of:
(a) determining the need to secure a patient to a spine board;
(b) placing a cervical collar, having a chin cup, on the patient's neck
(c) positioning the patient on a spine board;
(d) selecting device for stabilizing a patient's head on a spine board having a forehead strap, a chin strap, a crown strap, a lateral stabilization strap and a head harness having an interior surface and an exterior surface;
the head harness further having a main panel, two side panels each extending laterally from the main panel such that one side panel extends from each side of the main panel, two attachment straps each extending laterally from the head harness, a support cushion on the interior surface of the main panel, and a skid plate on the exterior surface of the main panel;
each of the attachment straps being secured to the head harness and having a free end opposite the main panel of the head harness;
the skid plate having a plurality of runners running longitudinally along the lower surface of the skid plate and the runners being adapted for low friction engagement with a spine board under the patient's head;
(e) properly aligning the head harness on the spine board;
(f) attaching the head harness to the spine board with the attachment straps;
(g) determining the required length of the forehead strap;
(h) adjusting the length of the forehead strap;
(i) attaching one end of the forehead strap to the head harness;
(j) securing the forehead strap to the patient's forehead;
(k) attaching the other end of the forehead strap to the head harness;
(l) placing the chin strap under the chin cup of the cervical collar;
(m) attaching the ends of the chin strap to the head harness;
(n) placing the crown strap across the crown of the patient's head;
(o) attaching the ends of the crown strap to the head harness;
(p) attaching the center of the lateral stabilization strap to the forehead strap at the center of the patient's forehead;
(q) attaching the ends of the lateral stabilization strap to the attachment straps;
whereby the patient's head will be immobilized and stabilized such that it cannot move laterally or be elevated; and
the patient's head can move longitudinally or rotate off of the longitudinal axis in conjunction with the patient's body.

4. The method of claim 3 wherein there is a layer of adhesive covering an area at the free end of the attachment straps on the lower surface of the attachment straps, the layer of adhesive having an easily removable protective cover;
the head harness is properly aligned on the spine by placing the harness underneath the patients head with the skid pad facing the spine board such that the attachment straps are even with the patient's eyes; and
the head harness is attached to the spine board by removing the protective cover from the layer of adhesive on each attachment strap, placing the adhesive material in contact with the spine board and applying pressure to the attachment straps.

5. The method of claim 3 wherein there is a portion of hook in loop material located on the interior surface of the side panels, the forehead strap has hook in loop material located on the surface of the forehead strap that will not be facing the forehead of the patient on the spine board, and a layer of adhesive material located on the surface of the forehead strap that will be facing the forehead of the patient on the spine board, the layer of adhesive having an easily removable protective cover; and
the length of the forehead strap is adjusted by cutting the forehead to a desired length, the forehead strap is attached to the head harness by engaging the hook in loop material on the exterior surface of the side panels with the hook in loop material on the forehead strap; and
the forehead strap is secured to the patient's forehead by removing the protective cover from the layer of adhesive on the forehead strap and forehead strap firmly placing the adhesive material in contact with the patient's forehead.

6. The method of claim 3 wherein there is a portion of hook in loop material located on the exterior surface of the side panels, a portion of hook in loop material located at the ends of the chin strap on the surface of the chin strap that will be facing the patient on the spine board, and a portion of hook in loop material located at the ends of the crown strap on the surface of the crown strap that will be facing a patient on a spine board;
the ends of the chin strap are attached to the head harness by engaging the hook in loop material on the exterior surface of the side panels with the hook in loop material on the chin strap; and
the ends of the crown strap are attached to the head harness by engaging the hook in loop material on the exterior surface of the side panels with the hook in loop material on the crown strap.

7. The method of claim 3 wherein there is a portion of hook in loop material on the upper surface of the end of the attachment straps that is opposite the main panel of the head harness and the lateral stabilization strap has hook in loop material located on the surface of the lateral stabilization strap that will be facing the forehead of a patient on a spine board;
the center of the lateral stabilization strap is attached to the forehead strap by engaging the hook in loop material on the lateral stabilization strap with the hook in loop material on the forehead strap; and
the lateral stabilization strap is attached to the attachment straps by engaging the hook in loop material on the lateral stabilization strap with the hook in loop material on the attachment straps.

* * * * *